US012605551B2

(12) United States Patent
Yu et al.

(10) Patent No.: US 12,605,551 B2
(45) Date of Patent: Apr. 21, 2026

(54) ELECTRICAL TREATMENT DEVICE

(71) Applicants: National University Corporation Chiba University, Chiba (JP); OMRON HEALTHCARE CO., LTD., Muko (JP)

(72) Inventors: Wenwei Yu, Chiba (JP); Siyu He, Chiba (JP); Shozo Takamatsu, Kyoto (JP)

(73) Assignees: National University Corporation Chiba University, Chiba (JP); OMRON HEALTHCARE CO., LTD., Kyoto (JP)

( * ) Notice: Subject to any disclaimer, the term of this patent is extended or adjusted under 35 U.S.C. 154(b) by 383 days.

(21) Appl. No.: 17/955,611

(22) Filed: Sep. 29, 2022

(65) Prior Publication Data

US 2023/0025216 A1    Jan. 26, 2023

Related U.S. Application Data

(63) Continuation of application No. PCT/JP2021/010819, filed on Mar. 17, 2021.

(30) Foreign Application Priority Data

Apr. 3, 2020    (JP) ................................. 2020-067568

(51) Int. Cl.
*A61N 1/36* (2006.01)
*A61N 1/05* (2006.01)

(52) U.S. Cl.
CPC ..... *A61N 1/36178* (2013.01); *A61N 1/36071* (2013.01); *A61N 1/0558* (2013.01)

(58) Field of Classification Search
CPC ............ A61N 1/36178; A61N 1/36071; A61N 1/0558
See application file for complete search history.

(56) References Cited

U.S. PATENT DOCUMENTS 8,521,291 B1 * 8/2013 Cholette ............ A61N 1/36053
                                                         607/40
2002/0055762 A1    5/2002  Gliner
                  (Continued)

FOREIGN PATENT DOCUMENTS

CN        110809486 A      2/2020
DE         10201320 A1     9/2002
                  (Continued)

OTHER PUBLICATIONS

Official Communication issued in corresponding Japanese Patent Application No. 2020-067568, mailed on Oct. 24, 2023.

(Continued)

*Primary Examiner* — Unsu Jung
*Assistant Examiner* — Natasha Patel
(74) *Attorney, Agent, or Firm* — Keating & Bennett, LLP

(57) ABSTRACT

An electrical treatment device includes: a plurality of electrodes to be in contact with a part of a body of a user; and a controller that performs a treatment onto the part by applying, to the plurality of electrodes, a burst wave that is constituted of a continuous wave of a plurality of pulses. The controller outputs a first burst wave including a plurality of pulses each having a first amplitude, and after outputting the first burst wave, controller repeatedly outputs a second burst wave including a plurality of positive pulses each having a second amplitude and a third burst wave including a plurality of negative pulses having a third amplitude. The first amplitude is larger than each of the second amplitude and the third amplitude.

3 Claims, 8 Drawing Sheets

(56)          References Cited

U.S. PATENT DOCUMENTS

| | | | |
|---|---|---|---|
| 2006/0293724 A1* | 12/2006 | Kronberg ............... | C12M 35/02 607/51 |
| 2008/0058871 A1 | 3/2008 | Libbus et al. | |
| 2011/0174235 A1* | 7/2011 | Vinano ................. | A01K 79/02 119/712 |
| 2011/0184488 A1* | 7/2011 | De Ridder ......... | A61N 1/36153 607/46 |
| 2014/0180361 A1 | 6/2014 | Burdick et al. | |
| 2016/0074664 A1* | 3/2016 | De Ridder .......... | A61N 1/0551 607/59 |
| 2016/0158550 A1* | 6/2016 | Hou ................... | A61N 1/36071 607/46 |
| 2017/0348530 A1* | 12/2017 | Doan ................. | A61N 1/36164 |
| 2018/0326220 A1 | 11/2018 | Kaula et al. | |
| 2019/0329025 A1 | 10/2019 | Moffitt et al. | |
| 2021/0101007 A1* | 4/2021 | Hamner ............... | A61B 5/4035 |
| 2021/0170179 A1* | 6/2021 | Lee ................... | A61N 1/36178 |
| 2022/0241589 A1* | 8/2022 | Crosby ............. | A61N 1/36021 |

FOREIGN PATENT DOCUMENTS

| | | | |
|---|---|---|---|
| JP | 2004-510562 A | 4/2004 |
| JP | 2010-502271 A | 1/2010 |
| JP | 2014-514043 A | 6/2014 |
| JP | 2017-192545 A | 10/2017 |
| WO | 2018009680 A1 | 1/2018 |

OTHER PUBLICATIONS

Official Communication issued in International Patent Application No. PCT/JP2021/010819, mailed on Apr. 27, 2021.

Official Communication issued in corresponding Chinese Patent Application No. 202180024767.6, mailed on Jul. 12, 2025, 9 pages.

Official Communication issued in corresponding German Patent Application No. 11 2021 002 158.3, issued on Nov. 24, 2025, 6 pages.

* cited by examiner

ELECTRICAL TREATMENT DEVICE

CROSS REFERENCE TO RELATED APPLICATIONS

The present application is a continuation of International application No. PCT/JP2021/010819, filed Mar. 17, 2021, which claims priority to Japanese Patent Application No. 2020-067568, filed Apr. 3, 2020, the entire contents of each of which are incorporated herein by reference.

BACKGROUND OF THE INVENTION

Field of the Invention

The present disclosure relates to an electrical treatment device.

Description of the Background Art

Conventionally, an electrical treatment device for alleviating stiffness and pain has been known. Such an electrical treatment device provides stimulation by bringing an electrode into contact with an affected part and outputting an electric signal to a muscle or the like through the electrode. For example, Japanese National Patent Publication No. 2014-514043 (PTL 1) discloses a stimulator device. This stimulator device transmits a complicated stimulation pattern to a selected electrode and modifies the complicated stimulation pattern based on a signal received from a sensor interface.

CITATION LIST

PTL 1: Japanese National Patent Publication No. 2014-514043

SUMMARY OF THE INVENTION

Technical Problem

Nerve fibers include: a myelinated nerve having a myelin sheath on an axon; and an unmyelinated nerve having no myelin sheath thereon. There has been known a treatment to induce a pain relieving effect in the following manner an electric current is made to flow through a needle to stimulate this unmyelinated nerve. However, in the conventional, ordinary electric stimulation through the electrode, the myelinated nerve, which is thick, is stimulated and excited, thus making it difficult to effectively excite the unmyelinated nerve, which is thin.

It is an object of a certain aspect of the present disclosure to provide an electrical treatment device so as to suppress excitation of a myelinated nerve and more effectively excite an unmyelinated nerve.

Solution to Problem

In one example of the present disclosure, there is provided an electrical treatment device including: a plurality of electrodes to be in contact with a part of a body of a user; and a controller that performs a treatment onto the part by applying, to the plurality of electrodes, a burst wave that is constituted of a continuous wave of a plurality of pulses. The controller outputs a first burst wave including a plurality of pulses each having a first amplitude, and after outputting the first burst wave, the controller repeatedly outputs a second burst wave including a plurality of positive pulses each having a second amplitude and a third burst wave including a plurality of negative pulses each having a third amplitude. The first amplitude is larger than each of the second amplitude and the third amplitude.

According to the above configuration, the excitation of the myelinated nerve can be suppressed and the unmyelinated nerve can be excited more effectively.

In another example of the present disclosure, the first amplitude is an amplitude corresponding to a current density of 29 mA/cm² or more.

According to the above configuration, the effect of suppressing the excitation of the myelinated nerve can be further increased.

In another example of the present disclosure, a repetition frequency of each pulse included in the first burst wave is 100 kHz or less.

According to the above configuration, the effect of suppressing the excitation of the myelinated nerve can be further increased.

In another example of the present disclosure, a length of the first burst wave is 20 ms or more.

According to the above configuration, the effect of suppressing the excitation of the myelinated nerve can be further increased.

In another example of the present disclosure, the second amplitude, a length of the second burst wave, the third amplitude, and a length of the third burst wave are set such that a total area of the positive pulses included in the second burst wave is equal to a total area of the negative pulses included in the third burst wave.

According to the above configuration, total net charge applied to the user can be zero.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a diagram showing a relation between a current density corresponding to an amplitude of a pre-burst wave and an excitation threshold value.

FIG. 6 is a diagram showing a relation between a carrier frequency of the pre-burst wave and the excitation threshold value.

DESCRIPTION OF THE PREFERRED EMBODIMENTS

Figure 1:
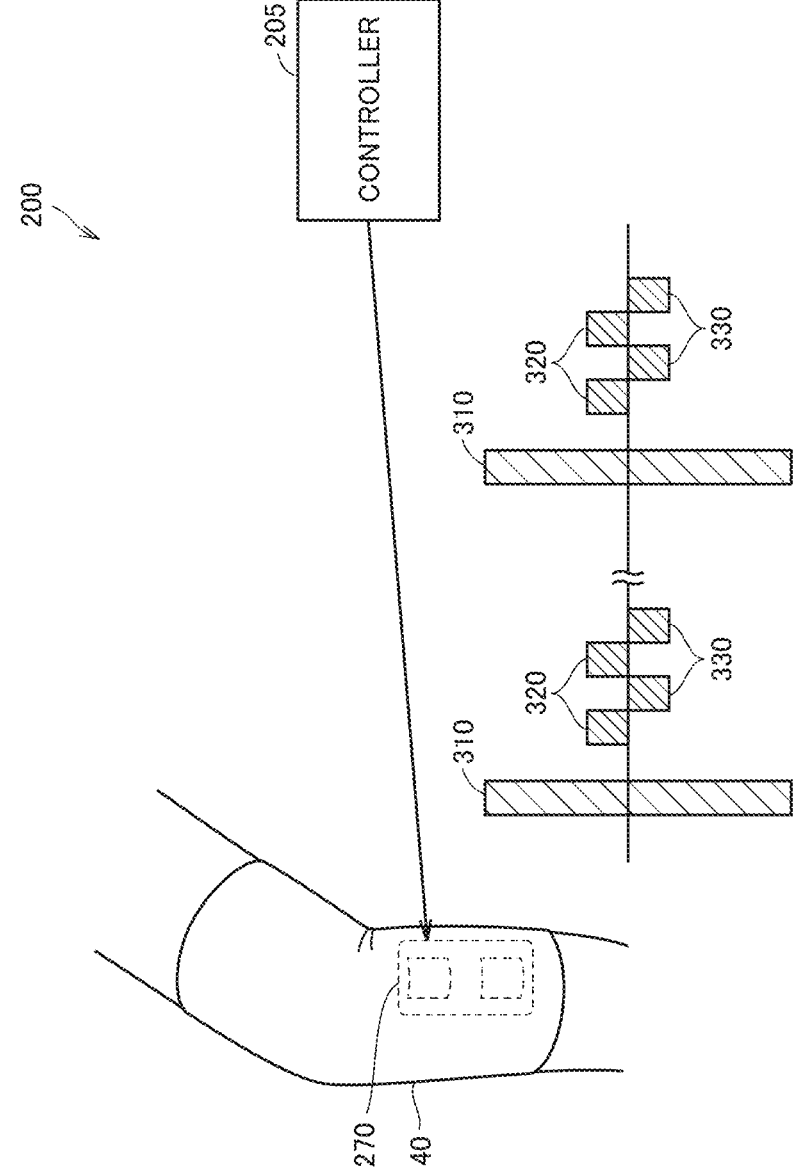
FIG. 1 is a diagram showing an electrical treatment device according to the present embodiment.

Hereinafter, embodiments of the present disclosure will be described with reference to figures. In the description below, the same components are denoted by the same reference characters. Their names and functions are also the same. Therefore, they will not be described in detail repeatedly.

[Exemplary Application]

An exemplary application of the present disclosure will be described with reference to FIG. 1. FIG. 1 is a diagram showing an electrical treatment device 200 according to the present embodiment.

Referring to FIG. 1, electrical treatment device 200 includes: a controller 205 serving as a main body portion; and a pair of pads 270 to be attached to a treatment-target part (for example, a part of a knee). Controller 205 and each of pads 270 are electrically connected to each other by a cord. A supporter 40 is a knee supporter that covers the entire knee of the user.

Electrical treatment device 200 is, for example, a low-frequency treatment device that supplies a low-frequency pulse current to perform therapies such as alleviation of pain of the knee of the user and relieving of shoulder stiffness. The frequency of the low-frequency pulse current is, for example, 1 Hz to 1200 Hz.

Pad 270 has a sheet-like shape and is attachable to the body of the user. Pad 270 has one surface (surface not to be in contact with the body) provided with a plug corresponding to an electrode (not shown) formed on the other surface (surface to be in contact with the body) of pad 270. The electrode is composed of, for example, an electrically conductive gel material or the like.

Controller 205 controls a pulse voltage to be applied to each of the electrodes of the pair of pads 270 that are in contact with the part (for example, knee) of the body of the user. Controller 205 applies, to the electrodes of pads 270, a burst wave that is constituted of a continuous wave of a plurality of pulses, thereby performing a treatment on the part.

Specifically, controller 205 outputs a pre-burst wave 310 including a plurality of pulses each having a large amplitude, and then outputs a main burst wave including a plurality of pulses each having a small amplitude. The main burst wave is a burst wave including pulses for the treatment on the part, and is constituted of: a positive burst wave 320 including a plurality of pulses (positive pulses) each having a positive polarity; and a negative burst wave 330 including a plurality of pulses (negative pulses) each having a negative polarity. Positive burst wave 320 and negative burst wave 330 are repeatedly output. By outputting the pre-burst wave having a large amplitude and then outputting the main burst wave having a small amplitude in this way, the excitation of the myelinated nerve can be suppressed and the unmyelinated nerve can be stimulated effectively. A reason for this will be described later in detail.

With the above control, in the electrical treatment device that performs a treatment with the pair of pads being attached to a treatment-target part, the excitation of the myelinated nerve can be suppressed, thereby effectively stimulating the unmyelinated nerve.

[Exemplary Configuration]

(External Appearance)

Figure 2:
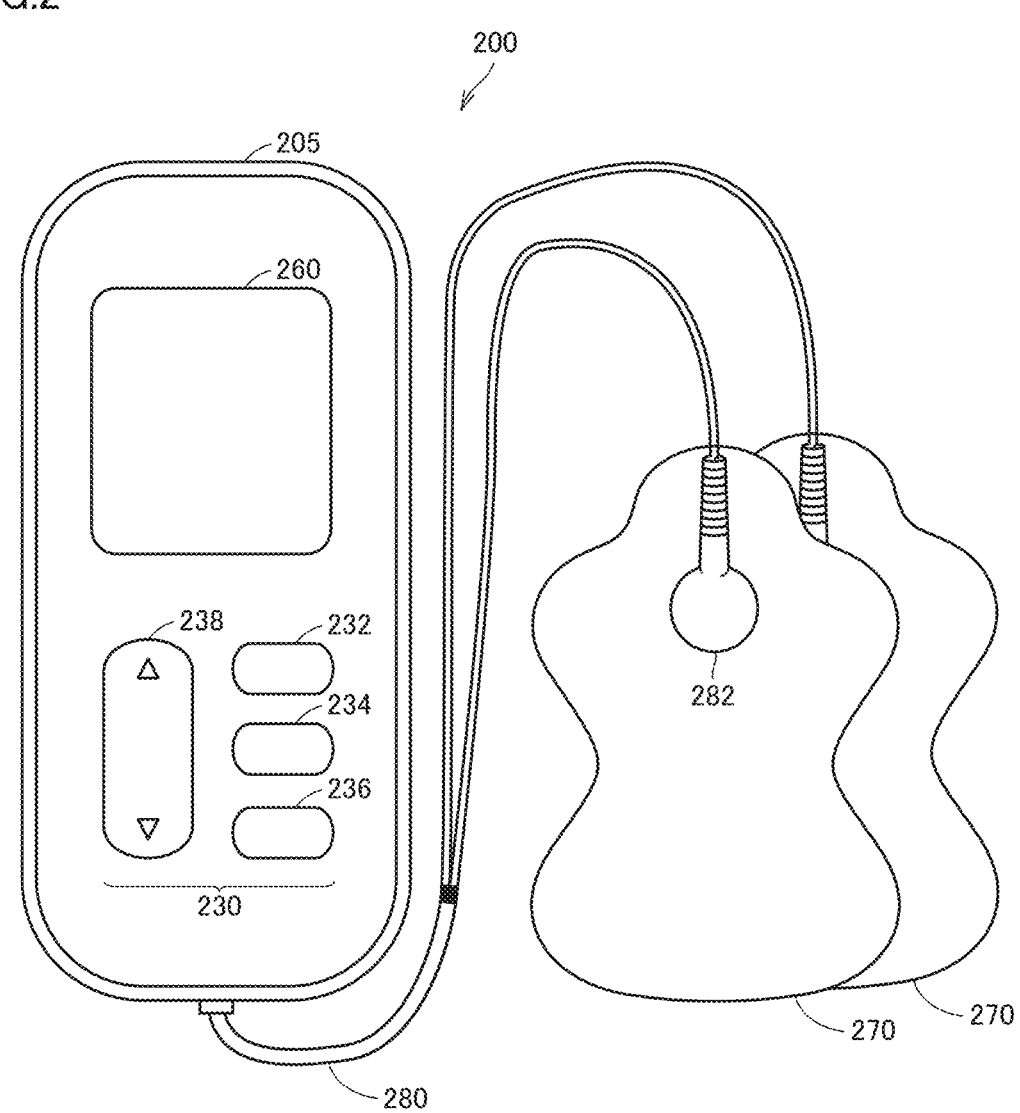
FIG. 2 is a diagram showing an exemplary external appearance of the electrical treatment device.

FIG. 2 is a diagram showing an exemplary external appearance of electrical treatment device 200. Referring to FIG. 2, electrical treatment device 200 includes controller 205, the pair of pads 270, and a cord 280 for electrically connecting controller 205 to each of pads 270.

A plug 282 of cord 280 is connected to a plug on the pad 270 side, and cord 280 is inserted into a jack of controller 205, thereby connecting controller 205 and pad 270 to each other. It should be noted that when the polarity of the electrode formed on one pad 270 is positive, the polarity of the electrode formed on the other pad 270 is negative.

Controller 205 is provided with: an operation interface 230 including various types of buttons; and a display 260. Operation interface 230 includes: a power supply button 232 for switching ON/OFF of a power supply; a mode selection button 234 for selecting a treatment mode; a treatment start button 236; and an adjustment button 238 for adjusting electric stimulation intensity. It should be noted that operation interface 230 is not limited to the above configuration, and may further include other buttons, dials, switches, or the like, for example.

Display 260 displays the electric stimulation intensity, the remaining time of the treatment, the treatment mode, the attachment state of pad 270, and the like, and displays various types of messages.

(Hardware Configuration)

Figure 3:
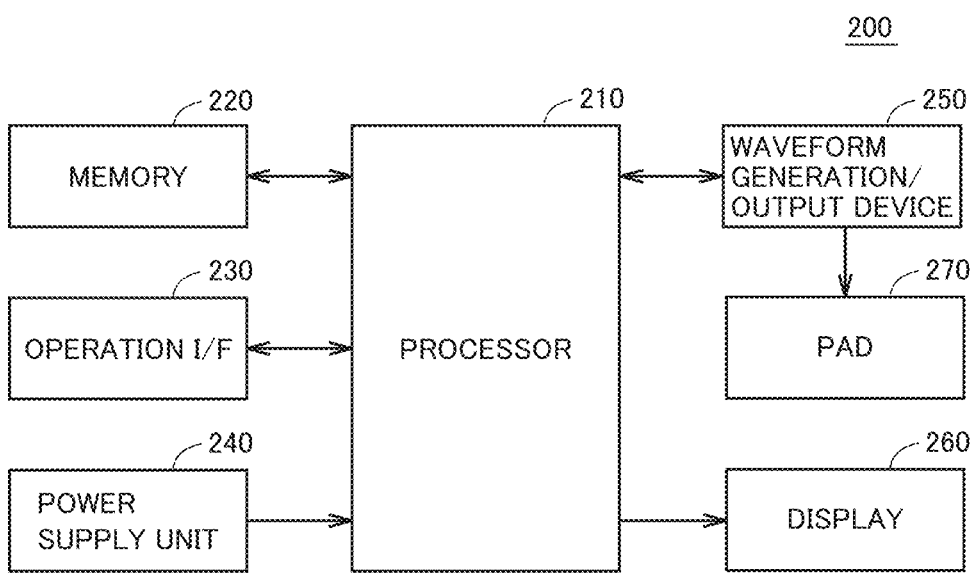
FIG. 3 is a block diagram showing an exemplary hardware configuration of the electrical treatment device.

FIG. 3 is a block diagram showing an exemplary hardware configuration of electrical treatment device 200. Referring to FIG. 3, controller 205 of electrical treatment device 200 includes a processor 210, a memory 220, operation interface (I/F) 230, a power supply unit 240, a waveform generation/output device 250, and display 260. Controller 205 is connected to the pair of pads 270.

Processor 210 is typically an arithmetic processing unit such as a CPU (Central Processing Unit) or an MPU (Multi Processing Unit). Processor 210 reads and executes a program stored in memory 220 so as to function as a control unit that controls an operation of each unit of electrical treatment device 200. Processor 210 executes the program so as to implement each of below-described processes (steps) of electrical treatment device 200.

Memory 220 is realized by a RAM (random access memory), a ROM (read-only memory), a flash memory, or the like. Memory 220 stores a program to be executed by processor 210, data to be used by processor 210, or the like.

Operation interface 230 receives an operation input onto electrical treatment device 200, and includes the various types of buttons as described above. When each of the various types of buttons is operated by the user, a signal corresponding to the operation is input to processor 210.

Power supply unit 240 supplies power to each component of electrical treatment device 200. As the power supply, for example, an alkaline dry battery or a secondary battery such as a lithium ion battery or a nickel-metal hydride battery is used, and a battery voltage is stabilized to generate a driving voltage to be supplied to each component.

Processor 210 controls a voltage to be applied to pad 270 via waveform generation/output device 250 so as to perform the treatment onto the treatment-target part. Specifically, in accordance with an instruction from processor 210, waveform generation/output device 250 outputs a current to flow through the treatment-target part of the body of the user via pad 270. Waveform generation/output device 250 includes a booster circuit, a voltage adjustment circuit, an output circuit, a current detection circuit, and the like.

The booster circuit boosts the power supply voltage to a predetermined voltage. The voltage adjustment circuit adjusts the voltage boosted by the booster circuit to a voltage corresponding to the electric stimulation intensity. Specifically, in electrical treatment device 200, adjustment button 238 can be used to set and adjust the electric stimulation intensity among a predetermined number of levels (for example, 20 levels). Processor 210 receives the setting input of the electric stimulation intensity via adjustment button 238, and instructs waveform generation/output device 250

(voltage adjustment circuit) to adjust the voltage to a voltage corresponding to the received electric stimulation intensity.

The output circuit generates a treatment waveform (pulse waveform) corresponding to the treatment mode based on the voltage adjusted by the voltage adjustment circuit, and outputs the treatment waveform to (the electrode of) pad 270 via cord 280. Specifically, when the user performs an operation such as switching of the treatment mode or changing of the electric stimulation intensity via operation interface 230, a control signal corresponding to the content of the operation is input from processor 210 to the output circuit. The output circuit outputs a treatment waveform corresponding to the control signal.

In electrical treatment device 200, a plurality of treatment modes are prepared in advance. Examples of the treatment modes prepared include: normal treatment modes such as a "massaging" mode, a "tapping" mode and a "pressing" mode; and a treatment mode (hereinafter, also referred to as "treatment mode M") to suppress the excitation of the myelinated nerve and more effectively stimulate the unmyelinated nerve so as to induce a pain relieving effect.

The output circuit can generate an electric stimulation corresponding to each mode by changing the waveform (including pulse width, pulse interval, frequency, output polarity) of the pulse or the like. The output circuit adjusts the electric stimulation intensity by changing the amplitude of the pulse voltage.

The current detection circuit detects a value of a current flowing between the pair of pads 270, and inputs, to processor 210, a signal indicating the detected value. Processor 210 can use the current value input from the current detection circuit to detect whether pads 270 are attached to the user or are not attached to the user. For example, when the current value is a predetermined value or more, processor 210 determines that the plurality of electrodes are in contact with the user (i.e., the pair of pads 270 are attached to the user), whereas when the current value is less than the predetermined value, processor 210 determines that at least one of the plurality of electrodes is not in contact with the user (i.e., at least one of the pair of pads 270 is not attached to the user).

Display 260 is constituted of, for example, an LCD (liquid crystal display), and displays various types of information in accordance with instructions from processor 210.

(As to Burst Wave)

Each of the burst waves used in treatment mode M will be described in more detail.

Figure 4:
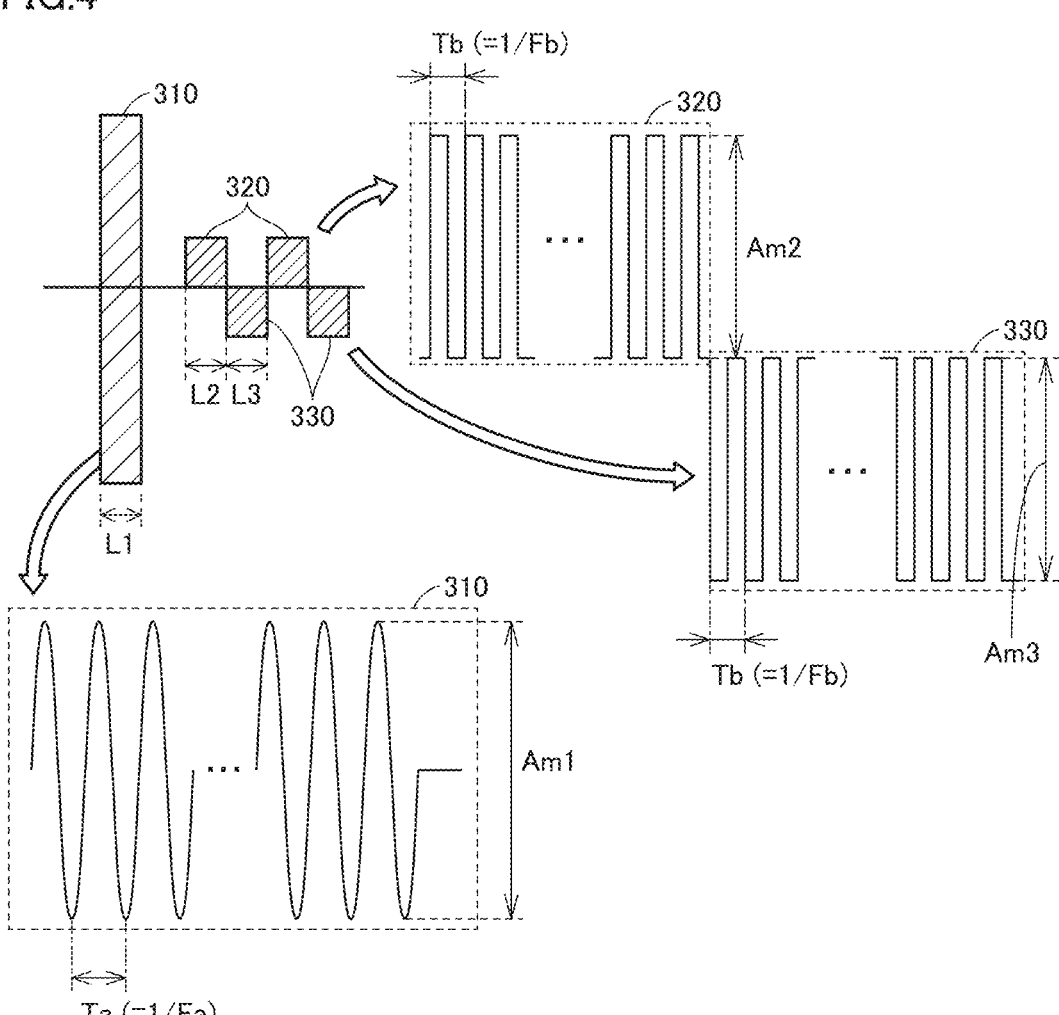
FIG. 4 is a diagram for illustrating burst waves used for treatment.

FIG. 4 is a diagram for illustrating the burst waves used for treatment. Referring to FIG. 4, pre-burst wave 310 is constituted of a plurality of pulse waves continuously generated at a pulse repetition cycle Ta. The repetition frequency of each pulse included in pre-burst wave 310 is defined as Fa (=1/Ta), and the amplitude of the pulse (the amplitude of pre-burst wave 310) is defined as Am1. Further, the burst length of pre-burst wave 310 (i.e., the length of the burst wave) is defined as L1. Hereinafter, the repetition frequency of each pulse included in the burst wave will be also referred to as "carrier frequency".

After outputting pre-burst wave 310, the main burst wave including positive burst wave 320 and negative burst wave 330 is output. In the example of FIG. 4, the main burst wave is output after passage of a certain period of time from the output of pre-burst wave 310; however, the main burst wave may be output immediately after the output of pre-burst wave 310.

Positive burst wave 320 is constituted of a plurality of positive pulse waves continuously generated at a pulse repetition cycle Tb. The carrier frequency of a positive pulse included in positive burst wave 320 is defined as Fb (=1/Tb), and the amplitude of the positive pulse (the amplitude of positive burst wave 320) is defined as Am2 The burst length of positive burst wave 320 is defined as L2. Negative burst wave 330 is constituted of a plurality of negative pulses continuously generated at pulse repetition cycle Tb. That is, the carrier frequency of the negative pulse included in negative burst wave 330 is Fb, which is equal to the carrier frequency of positive burst wave 320. Further, the amplitude of the negative pulse (the amplitude of negative burst wave 330) is defined as Am3, and the burst length of negative burst wave 330 is defined as L3.

The area of each positive pulse is found by "amplitude Am2×positive pulse width", and the area of each negative pulse is found by "amplitude Am3× negative pulse width". The positive pulse width and the negative pulse width are equal to each other. Further, the total area of the positive pulses included in positive burst wave 320 (i.e., the total value of the areas of the positive pulses) and the total area of the negative pulses included in negative burst wave 330 (i.e., the total value of the areas of the negative pulses) are set to be equal to each other. Thus, the total net charge applied to the user can be effectively zero (i.e., an amount of positive charges and an amount of negative charges can be balanced).

In the present embodiment, the carrier frequencies of the positive pulse and the negative pulse are set to be the same, i.e., Fb (for example, 10 kHz). Therefore, amplitudes Am2, Am3 and burst lengths L2, L3 are set such that the total area of the positive pulses is equal to the total area of the negative pulses. As a specific example, amplitudes Am2, Am3 are set to be the same (for example, an amplitude corresponding to a current density of "1 mA/cm$^2$"), and burst lengths L2, L3 are also set to be the same (for example, 5 ms). The repetition cycle (i.e., corresponding to L2+L3) of the main burst wave is, for example, 10 ms, and the repetition frequency is 100 Hz. It should be noted that since electrical treatment device 200 is a low-frequency treatment device, the repetition frequency is included in a range of 1 Hz to 1200 Hz.

Here, a method of setting amplitude Am1 of the pulse included in pre-burst wave 310, carrier frequency Fa, and burst length L1 will be described with reference to FIGS. 5 to 7.

Figure 5:
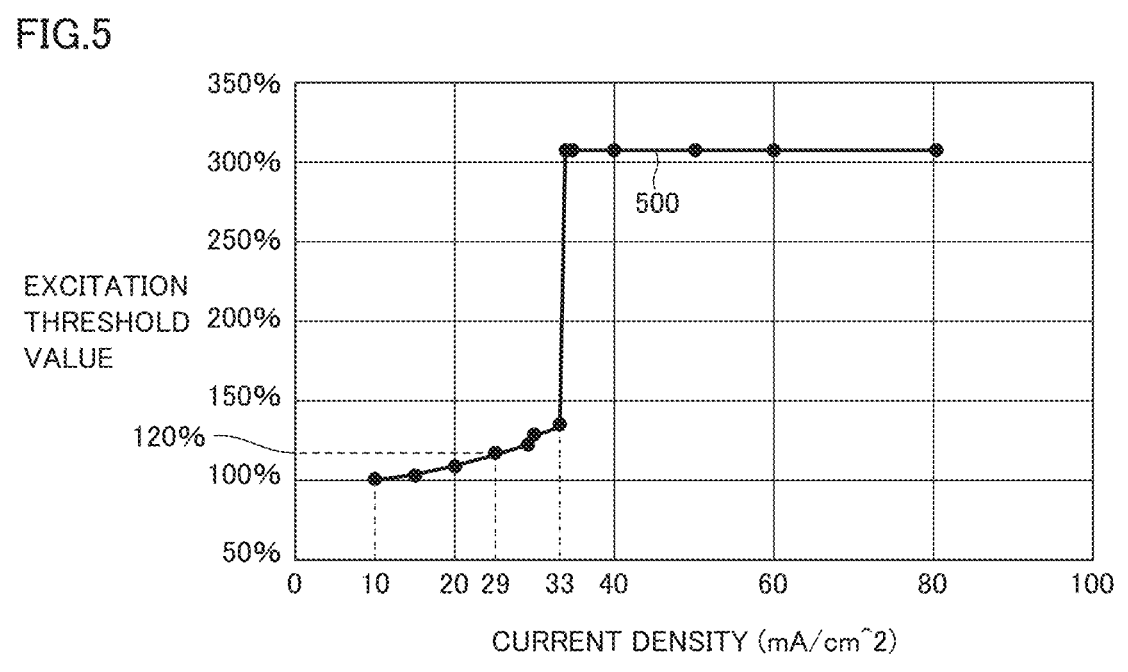

FIG. 5 is a diagram showing a relation between a current density corresponding to the amplitude of the pre-burst wave and an excitation threshold value. In FIG. 5, the carrier frequency of the pre-burst wave is set to 100 kHz, the burst length is set to 20 ms (milliseconds), and the amplitude corresponding to the current density is changed.

Referring to FIG. 5, the excitation threshold value is an index indicating a degree of suppression of excitation of the myelinated nerve. A higher excitation threshold value indicates that the myelinated nerve is less likely to be excited (i.e., the excitation of the myelinated nerve is suppressed).

The amplitude (hereinafter, also referred to as "reference amplitude As") of the main burst wave when the action potential of the myelinated nerve is detected (the myelinated nerve is excited) without applying the pre-burst wave is checked. The excitation threshold value corresponding to the amplitude on this occasion is defined as "100%". For example, amplitude Ax1 of the main burst wave by which the myelinated nerve is excited after applying the pre-burst wave having an amplitude corresponding to a current density of "10 mA/cm$^2$" is checked. The excitation threshold value when the current density is "10 mA/cm$^2$" is represented by "(Ax1/As)×100%". According to a graph 500, it is indicated that when the current density is 10 mA/cm², the excitation threshold value is 100%, so that amplitude Ax1 and reference amplitude As are equal to each other. Therefore, it is understood that the excitation of the myelinated nerve is not suppressed in this case.

On the other hand, for example, amplitude Ax2 of the main burst wave when the myelinated nerve is excited after applying the pre-burst having an amplitude corresponding to a current density of 29 mA/cm² is checked. According to graph 500, it is indicated that when the current density is 29 mA/cm², the excitation threshold value is 120%, so that amplitude Ax2 is 1.2 times as large as reference amplitude As. Specifically, when the current density corresponding to the amplitude of the pre-burst wave is 29 mA/cm², the myelinated nerve is not excited unless the amplitude of the main burst wave is increased (specifically, by 20%) as compared with the case where the pre-burst wave is not applied. Therefore, it is understood that the excitation of the myelinated nerve is suppressed in this case.

According to graph 500, when the current density is 10 mA/cm² or less, the effect of suppressing the excitation of the myelinated nerve cannot be recognized; however, the effect of suppressing starts to be recognized when the current density becomes more than 10 mA/cm². When the current density becomes more than 33 mA/cm², the excitation threshold value becomes more than 300%, and the effect of suppressing the excitation of the myelinated nerve is abruptly increased and is then saturated.

Here, even when the amplitude of the pre-burst wave is changed, the amplitude of the main burst wave by which the action potential of the unmyelinated nerve is detected (i.e., the unmyelinated nerve is excited) is substantially unchanged. Therefore, by appropriately setting the amplitude of the pre-burst wave to suppress the excitation of the myelinated nerve, the unmyelinated nerve can be excited without exciting the myelinated nerve. It should be noted that in consideration of a design error or the like, practically, when the excitation threshold value is 120% or more, the unmyelinated nerve can be considered to be effectively excited while suppressing the excitation of the myelinated nerve. Therefore, amplitude Am1 of pre-burst wave 310 is preferably set to an amplitude corresponding to a current density of 29 mA/cm² or more.

Figure 6:
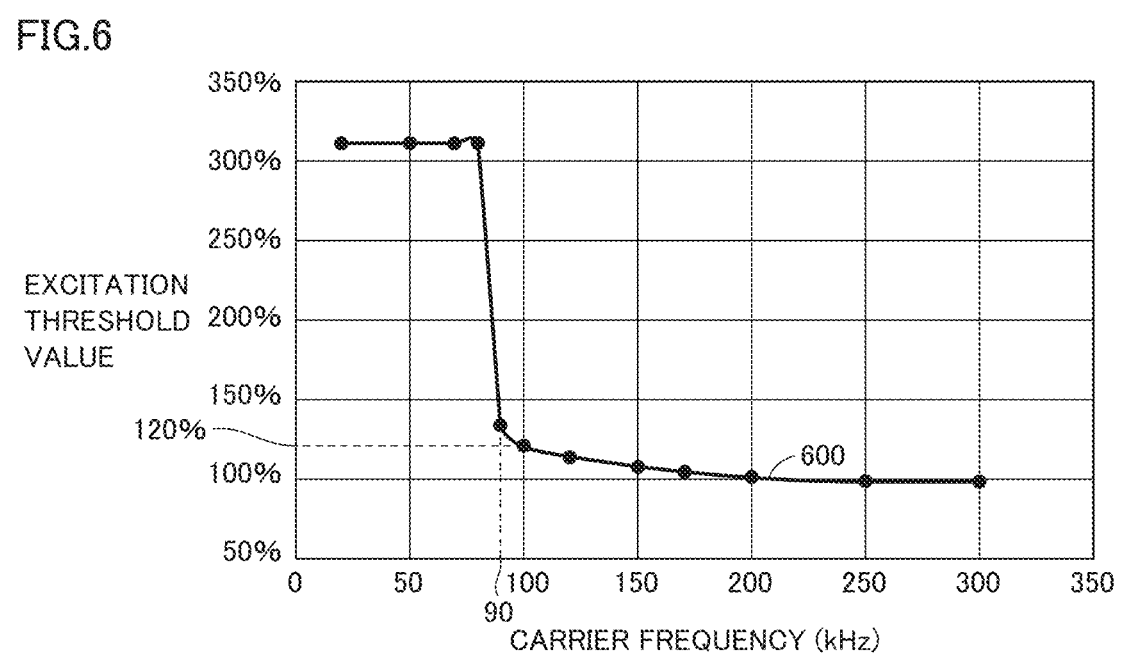

FIG. 6 is a diagram showing a relation between the carrier frequency of the pre-burst wave and the excitation threshold value. In FIG. 6, the current density corresponding to the amplitude of the pre-burst wave is set to 29 mA/cm², the burst length is set to 20 ms, and the carrier frequency is changed.

Referring to FIG. 6, for example, amplitude Ay1 of the main burst wave when the myelinated nerve is excited after applying the pre-burst wave having a carrier frequency of "300 kHz" is checked. The excitation threshold value on this occasion is represented as "(Ay1/As)×100%". According to a graph 600, when the carrier frequency is "300 kHz", the excitation threshold value is 100%, so that amplitude Ay1 and reference amplitude As are equal to each other. Therefore, the excitation of the myelinated nerve is not suppressed in this case.

On the other hand, for example, amplitude Ay2 of the main burst wave when the myelinated nerve is excited after applying the pre-burst wave having a carrier frequency of "100 kHz" is checked. According to graph 600, when the carrier frequency is "100 kHz", the excitation threshold value is 120%, so that amplitude Ay2 is 1.2 times as large as reference amplitude As. Specifically, when the carrier frequency of the pre-burst wave is "100 kHz", the myelinated nerve is not excited unless the amplitude of the main burst wave is increased (specifically, by 20%) as compared with the case where the pre-burst wave is not applied. Therefore, it is understood that the excitation of the myelinated nerve is suppressed in this case.

According to graph 600, when the carrier frequency is 200 kHz or more, the effect of suppressing the excitation of the myelinated nerve cannot be recognized; however, the effect of suppressing starts to be recognized when the carrier frequency becomes less than 200 kHz. When the frequency becomes less than 90 kHz, the excitation threshold value becomes more than 300%, and the effect of suppressing the excitation of the myelinated nerve is abruptly increased and is then saturated.

Here, even when the carrier frequency of the pre-burst wave is changed, the amplitude of the main burst wave by which the unmyelinated nerve is excited is substantially unchanged. Therefore, by appropriately setting the carrier frequency of the pre-burst wave to suppress the excitation of the myelinated nerve, the unmyelinated nerve can be excited without exciting the myelinated nerve. It should be noted that carrier frequency Fa of pre-burst wave 310 is preferably set to be less than or equal to 100 kHz corresponding to the excitation threshold value of "120%".

Figure 7:
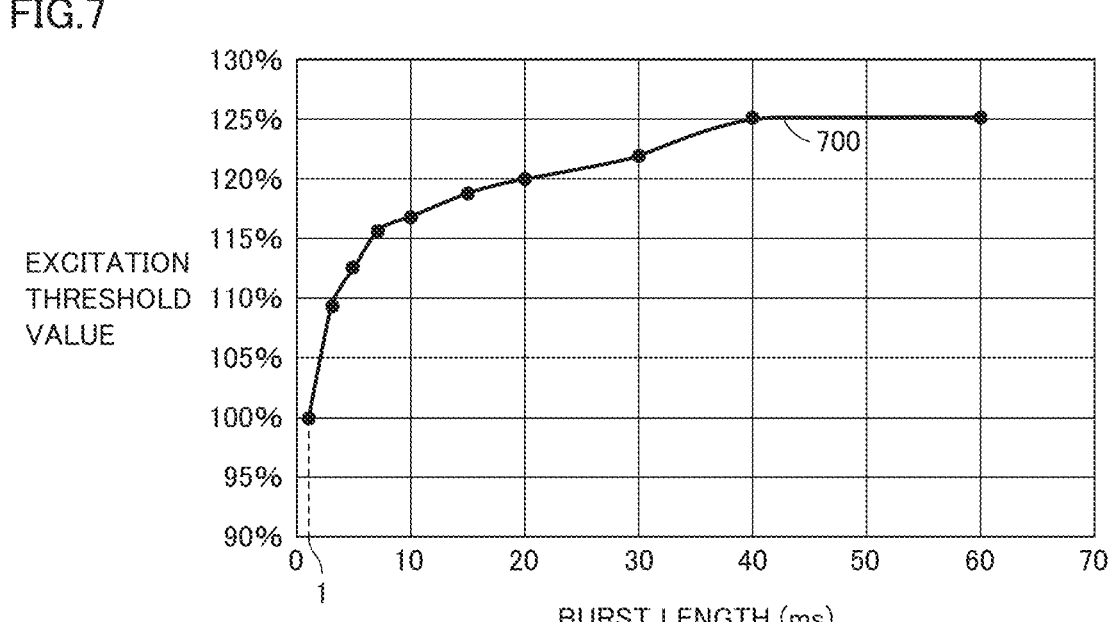
FIG. 7 is a diagram showing a relation between a burst length of the pre-burst wave and the excitation threshold value.

FIG. 7 is a diagram showing a relation between the burst length of the pre-burst wave and the excitation threshold value. In FIG. 7, the current density corresponding to the amplitude of the pre-burst wave is set to 29 mA/cm², the carrier frequency is set to 100 kHz, and the burst length is changed.

Referring to FIG. 7, for example, amplitude Az1 of the main burst wave when the myelinated nerve is excited after applying the pre-burst wave having a burst length of "1 ms" is checked. The excitation threshold value on this occasion is represented by "(Az1/As)×100%". According to a graph 700, when the burst length is "1 ms", the excitation threshold value is 100%, so that amplitude Az1 and reference amplitude As are equal to each other. Therefore, the excitation of the myelinated nerve is not suppressed in this case.

On the other hand, for example, amplitude Az2 of the main burst wave when the myelinated nerve is excited after applying the pre-burst having a burst length of "20 ms" is checked. According to graph 700, when the burst length is "20 ms", the excitation threshold value is 120%, so that amplitude Ay2 is 1.2 times as large as reference amplitude As. Specifically, when the burst length of the pre-burst wave is "20 ms", the myelinated nerve is not excited unless the amplitude of the main burst wave is increased by 20% as compared with the case where the pre-burst wave is not applied. Therefore, it is understood that the excitation of the myelinated nerve is suppressed in this case.

According to graph 700, as the burst length becomes more than 1 ms, the effect of suppressing the excitation of the myelinated nerve becomes more significant. When the burst length becomes 40 ms or more, the excitation threshold value is increased to 125% and is then saturated. Here, even when the burst length of the pre-burst wave is changed, the amplitude of the main burst wave by which the unmyelinated nerve is excited is substantially unchanged. Therefore, by appropriately setting the burst length of the pre-burst wave to suppress the excitation of the myelinated nerve, the unmyelinated nerve can be excited without exciting the myelinated nerve. It should be noted that burst length L1 of the pre-burst wave is preferably set to be more than or equal to 20 ms corresponding to the excitation threshold value of "120%".

The amplitude, carrier frequency, and burst length of each of the pre-burst wave and the main burst wave will be discussed. As illustrated above, it is assumed that the amplitude, carrier frequency, and burst length of the main burst wave are 1 mA/cm², 10 kHz, and 10 ms, respectively. Referring to FIGS. 5 to 7, in order to obtain the effect of suppressing the excitation of the myelinated nerve, the amplitude of the pre-burst wave needs to be larger than 10 mA/cm², the carrier frequency of the pre-burst wave needs to be smaller than 200 kHz, and the burst length of the pre-burst wave needs to be larger than 1 ms.

Therefore, in order to obtain the effect of suppressing the excitation of the myelinated nerve, the carrier frequency and burst length of the pre-burst wave may be the same as those of the main burst wave; however, the amplitude of the pre-burst wave needs to be larger than that of the main burst wave. In view of this, amplitude Am1 of pre-burst wave 310 is set to be larger than each of amplitude Am2 of positive burst wave 320 and amplitude Am3 of negative burst wave 330.

(Processing Procedure)

Figure 8:
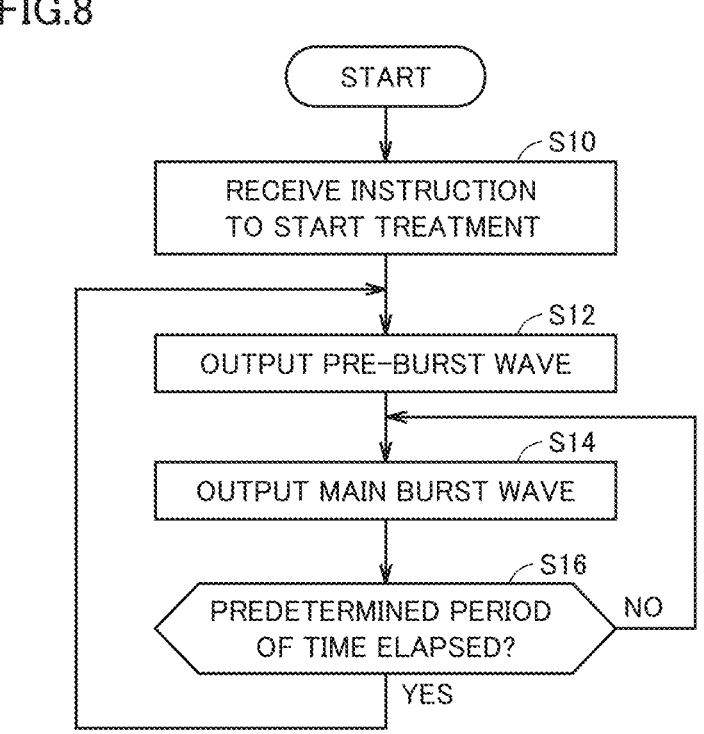
FIG. 8 is a flowchart showing an exemplary processing procedure of the electrical treatment device.

FIG. 8 is a flowchart showing an exemplary processing procedure of electrical treatment device 200. Each step in FIG. 8 is mainly performed by processor 210 of electrical treatment device 200. Here, it is assumed that a treatment in treatment mode M is performed.

Referring to FIG. 8, from the user via operation interface 230, electrical treatment device 200 receives an instruction to start a treatment in treatment mode M (step S10). Electrical treatment device 200 generates and outputs pre-burst wave 310 (step S12). After outputting pre-burst wave 310, electrical treatment device 200 repeatedly outputs the main burst wave at a predetermined frequency (for example, 100 Hz) (step S14).

Electrical treatment device 200 determines whether or not a predetermined period of time has elapsed from the output of pre-burst wave 310 (step S16). The predetermined period of time is set to such a period of time that the effect of suppressing the excitation of the myelinated nerve by pre-burst wave 310 can be maintained. Since the period of time during which the effect of suppressing can be maintained is varied depending on the amplitude, carrier frequency, and burst length of pre-burst wave 310, a predetermined period of time suitable for the setting of pre-burst wave 310 is set in advance.

When the predetermined period of time has not elapsed (NO in step S16), electrical treatment device 200 performs the process of step S14. That is, electrical treatment device 200 repeatedly outputs the main burst wave. When the predetermined period of time has elapsed (YES in step S16), electrical treatment device 200 performs the process of step S12. Specifically, electrical treatment device 200 stops outputting the main burst wave and outputs the pre-burst wave.

OTHER EMBODIMENTS (1) In the above-described embodiment, it has been illustrated that the pair of pads 270 are used; however, it is not limited to such a configuration, and an electrode for positive polarity and an electrode for negative polarity may be formed on one pad.

(2) In the above-described embodiment, it has been illustrated that the electrical treatment device solely performs the treatment onto the user; however, it is not limited to such a configuration, and a terminal device and an electrical treatment device may be wirelessly connected to each other and the electrical treatment device may perform a treatment in accordance with an instruction from the terminal device. In this case, the terminal device mainly plays the roles of operation interface 230 and display 260 of electrical treatment device 200.

Specifically, the electrical treatment device is of cordless type, has a pad, a holder, and a main body portion which are to be integrated when used, and performs a treatment in combination of these portions. The terminal device is, for example, a smartphone having a touch panel. For a network for connecting the terminal device to the electrical treatment device, for example, wireless communication methods such as Bluetooth (registered trademark), wireless LAN (Local Area Network), and other wireless communication methods are employed.

The terminal device uses an application installed thereon to provide various types of instructions to the electrical treatment device that is wirelessly connected thereto. Further, the terminal device displays various types of information on its display to notify necessary information to the user. The user provides various types of instructions to the terminal device via the touch panel and the instructions are transmitted from the terminal device to the electrical treatment device, thereby indirectly providing the various instructions to the electrical treatment device. More specifically, the electrical treatment device receives an instruction input from the user and transmitted from the terminal device. For example, the terminal device receives an operation of selecting a treatment mode or an operation of adjusting the electric stimulation intensity, and transmits a signal indicating the operation to the electrical treatment device. In accordance with the operation corresponding to the received signal, the electrical treatment device outputs a pulse wave corresponding to the selected treatment mode or adjusts the level of the electric stimulation intensity.

(3) In the above-described embodiment, it is also possible to provide a program that causes a computer to function to perform the control as described in the above-described flowchart. Such a program can be provided as a program product by recording the program on a non-transitory computer-readable recording medium accompanied with the computer, such as a flexible disk, a CD-ROM (Compact Disk Read Only Memory), a secondary storage device, a main storage device, or a memory card. Alternatively, the program can be provided by recording the program on a recording medium such as a hard disk included in the computer. The program can also be provided by downloading via a network.

(4) The configuration illustrated as the above-described embodiment is an exemplary configuration of the present disclosure, and can be combined with another known technology, or can be modified by omitting a part of the configuration without departing from the gist of the present disclosure. Further, in the above-described embodiment, the processing and configurations described in the other embodiments may be employed as appropriate for the sake of implementation.

Additional Notes

As described above, the present embodiment includes the following disclosure.

[Configuration 1]

An electrical treatment device (200) comprising: a plurality of electrodes to be in contact with a part of a body of a user; and a controller (205) that performs a treatment onto the part by applying, to the plurality of electrodes, a burst wave that is constituted of a continuous wave of a plurality of pulses, wherein the controller (205) outputs a first burst wave including a plurality of pulses each having a first amplitude, after outputting the first burst wave, the controller (205) repeatedly outputs a second burst wave including a plurality of positive pulses each having a second amplitude and a third burst wave including a plurality of negative pulses each having a third amplitude, and the first amplitude is larger than each of the second amplitude and the third amplitude.

[Configuration 2]

The electrical treatment device (200) according to configuration 1, wherein the first amplitude is an amplitude corresponding to a current density of 29 mA/cm$^2$ or more.

[Configuration 3]

The electrical treatment device (200) according to configuration 1 or 2, wherein a repetition frequency of each pulse included in the first burst wave is 100 kHz or less.

[Configuration 4]

The electrical treatment device (200) according to any one of configurations 1 to 3, wherein a length of the first burst wave is 20 ms or more.

[Configuration 5]

The electrical treatment device (200) according to any one of configurations 1 to 4, wherein the second amplitude, a length of the second burst wave, the third amplitude, and a length of the third burst wave are set such that a total area of the positive pulses included in the second burst wave is equal to a total area of the negative pulses included in the third burst wave.

Although the present invention has been described and illustrated in detail, it is clearly understood that the same is by way of illustration and example only and is not to be taken by way of limitation, the scope of the present invention being interpreted by the terms of the appended claims.

The invention claimed is:

1. An electrical treatment device comprising:

a plurality of electrodes to be in contact with a part of a body of a user; and a controller that performs a treatment onto the part by applying, to the plurality of electrodes, a first burst wave, a second burst wave, and a third burst wave, wherein the controller outputs the first burst wave constituted of a continuous wave of a plurality of pulses each having a first amplitude, after outputting the first burst wave, the controller repeatedly outputs the second burst wave constituted of a continuous wave of a plurality of positive pulses each having a second amplitude and the third burst wave constituted of a continuous wave of a plurality of negative pulses each having a third amplitude, and the first amplitude is larger than each of the second amplitude and the third amplitude, a repetition frequency of each pulse included in the first burst wave is 100 KHz or less, a length of the first burst wave is between 20 ms and 60 ms, and a repetition frequency of each positive pulse included in the second burst wave is equal to a repetition frequency of each negative pulse included in the third burst wave.

2. The electrical treatment device according to claim 1, wherein the second amplitude, a length of the second burst wave, the third amplitude, and a length of the third burst wave are set such that a total area of the positive pulses included in the second burst wave is equal to a total area of the negative pulses included in the third burst wave.

3. The electrical treatment device according to claim 1, wherein:

the second amplitude is equal to the third amplitude, and a length of the second burst wave is equal to a length of the third burst wave.

* * * * *